US006823286B2

(12) United States Patent
Yuste et al.

(10) Patent No.: US 6,823,286 B2
(45) Date of Patent: Nov. 23, 2004

(54) METHOD AND SYSTEM FOR ANALYZING MULTI-DIMENSIONAL DATA

(75) Inventors: Rafael Yuste, New York, NY (US); Vikram S. Kumar, Boston, MA (US); Robert C. Froemke, Oakland, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/297,160

(22) PCT Filed: Jun. 29, 2001

(86) PCT No.: PCT/US01/21032

§ 371 (c)(1),
(2), (4) Date: Jun. 26, 2003

(87) PCT Pub. No.: WO02/03327

PCT Pub. Date: Jan. 10, 2002

(65) Prior Publication Data

US 2004/0015310 A1 Jan. 22, 2004

Related U.S. Application Data

(60) Provisional application No. 60/214,914, filed on Jun. 29, 2000.

(51) Int. Cl.[7] .............................................. G06F 19/00
(52) U.S. Cl. ........................................ 702/179; 717/125
(58) Field of Search .................................. 702/179, 180, 702/181, 182, 187–188, 194, 196; 717/125, 127, 132, 134, 155

(56) References Cited

U.S. PATENT DOCUMENTS

| 5,215,099 A | | 6/1993 | Haberl et al. ............... 128/702 |
| 5,608,908 A | * | 3/1997 | Barghouti et al. .......... 719/318 |
| 6,064,770 A | * | 5/2000 | Scarth et al. ............... 382/225 |
| 6,525,712 B1 | * | 2/2003 | Held .......................... 345/156 |
| 6,728,955 B1 | * | 4/2004 | Berry et al. ................ 717/158 |

FOREIGN PATENT DOCUMENTS

WO          9944062         9/1999       .......... G01N/33/50

OTHER PUBLICATIONS

"A Tutorial on Hidden Markov Models and Selected Applications in Speech Recognition" by Lawrence R. Rabiner, *Proceedings of the IEEE*; vol. 77, No. 2, Feb. 1989, pp. 257–285.

(List continued on next page.)

*Primary Examiner*—Marc S. Hoff
*Assistant Examiner*—Edward Raymond
(74) *Attorney, Agent, or Firm*—Baker Botts L.L.P.

(57) ABSTRACT

Disclosed is a method for analyzing a sequence of data arrays. A selection of at least one type of region of interest and at least one region of interest from said data arrays is made. The sequence of data arrays are then transformed into a simplified data array. Events of interest in the selected regions of interest are then detected and stored in a second simplified data array. The data is then analyzed to determine relationships between the detected events of interest

39 Claims, 4 Drawing Sheets

OTHER PUBLICATIONS

"The Segmental K–Means Algorithm for Estimating Parameters of Hidden Markov Models" by Juang et al., *IEEE Transactions on Acoustics, Speech and Signal Processing*, vol. 38, No. 9, Sep. 1990, pp. 1639–1641.

"Hidden Markov Modelling of Simultaneously Recorded Cells in the Associative Cortex of Behaving Monkeys" by Gat et al., *Comput. Neural Sys*, vol. 8, 1997, pp. 297–322.

"Networks of Coactive Neurons in Developing Layer 1" by Schwartz et al., *Neuron*, vol. 20, Mar. 1998, pp. 541–552.

"Solution of Linear Algebraic Equations", Chapter 2.0 Introduction, by *Press Numerical Recipes in C*, 1992, pp. 29–31.

"Least–Squares Techniques" by Christopher Bishop, *Neural Network for Pattern Recognition*, 1995, p. 93, 171, an 260.

"Maximum–Likelihood Estimation for Mixture Multivariate Stochastic Observations of Markov Chains" by B. H. Juang, *AT&T Technical Journal*, vol. 64, No. 6, Jul.–Aug. 1985, pp. 1235–1249.

"Statistical Interference for Probabilistic Functions of Finite State of Markov Chains" by Baum et al., *Interference for Functions of Markov Chains*, 1966, pp. 1554–1563.

"Mixture Autoregressive Hidden Markov Models for Speech Signals" by Juang et al., *IEEE Transactions of Acoustics, Speech, and Processing*, vol. ASSP 33, No. 6, Dec. 1985, pp. 1404–1413.

"Maximum Likelihood Estimation for Multivariate Observations of Markov Sources" by Louis A. Liporace, *IEEE Transactions on Information Theory*, vol. IT–28, No. 5, Sep. 1982, pp. 729–734.

"Cluster Analysis and Data Visualization of Large–Scale Gene Expression Data" by George S. Michaels, Daniel B. Carr, Manor Askenazi, Stefanie Fuhrman, Xiling Wen, Roland Somogyi, XP–000974575, 1997, pp. 41–53.

\* cited by examiner

METHOD AND SYSTEM FOR ANALYZING MULTI-DIMENSIONAL DATA

RELATED APPLICATION

This application claims priority from U.S. provisional application No. 60/214,914 filed on Jun. 29, 2000, which is incorporated by reference herein in its entirety

BACKGROUND OF INVENTION

The present invention relates to analyzing and interpreting multi-dimensional datasets. Examples of such datasets include optical recordings of neuronal cell slice fluorescence and differences in expression levels of multiple genes within a population of patients or subjects.

It is often desirable to understand the relationship of various events occurring within such a multidimensional dataset. For example, various neurons in a neuronal cell slice may exhibit spontaneous activity in a time series of optical images. It would be desirable to determine which, if any, group of neurons were ever coactive (i.e. active at the same time or at specific different times), were regularly coactive (i.e. coactive at multiple times over the period of observation), and which neuron, if any, consistently activates before or after another neuron activates. It would also be advantageous to know the statistical significance of the relationships between the various events. In other words, whether the correlation among the various events is stronger than would be expected from random activity.

SUMMARY OF THE INVENTION

These and other advantages are achieved by the present invention which provides a method and system for analyzing a multidimensional dataset and for detecting relationships between various events reflected in the dataset.

In an exemplary embodiment, a method is presented for analyzing a sequence of data arrays including selecting at least one type of region of interest and at least one region of interest for each type of region of interest chosen from said data arrays, and transforming the sequence of data arrays into a simplified data array with a first dimension equal to the number of selected regions of interest and a second dimension equal to the number of data arrays in the original sequence of data arrays. The simplified data array is then examined to detect events of interest in the regions of interest, and those events of interest are stored in a second simplified data array having the same dimensions as the first simplified data array, but the data in each element of the array is binary. The second simplified array is then analyzed to determine relationships between the events of interest and correspondingly, the regions of interest.

In one exemplary embodiment, analyzing includes plotting a portion or all of the data in the first simplified array to allow visual examination of the relationships between the activities of interest in various regions of interest. In another exemplary embodiment, the analysis step involves detecting events of interest that are coactive and determining whether the number of coactive events is statistically significant. This embodiment may include detecting all such coactive events (i.e. events where at least two regions of interest are active simultaneously), detecting instances where many regions of interest are coactive simultaneously, or detecting instances where two or more regions of interest are each active in a certain temporal relationship with respect to one another (also referred to as coactivity).

In a further exemplary embodiment, the data analysis involves calculating a correlation coefficient between two regions of interest based on how often the regions of interest are coactive relative to how often the first region is active. A map of all such regions is displayed with lines between the regions having a thickness proportional to the correlation coefficient between the two regions.

Another exemplary embodiment includes plotting a cross-correlogram or histogram of events of interest in a particular region of interest with respect to events of interest in another region of interest, so that the histogram will reveal the number of times an event of interest in the first region of interest occurs a certain number of locations away from an event of interest in the second region of interest in the second simplified data array. The cross-correlogram can be plotted with respect to one region of interest, thus showing how many times an event of interest occurs before or after the occurance of another event of interest in the same region of interest.

Other exemplary embodiments include performing Hidden Markov Modeling on the second simplified data array to determine a hidden Markov state sequence and displaying a cross-correlogram between events of interest occurring in one region of interest while that region is in one of the detected Markov states and performing a singular value decomposition on the first simplified data array.

BRIEF DESCRIPTION OF THE DRAWINGS

For a more complete understanding of the present invention, reference is made to the following detailed description of a exemplary embodiments with reference to the accompanying drawings in which.

DESCRIPTION OF THE PREFERRED EMBODIMENT

Figure 1:
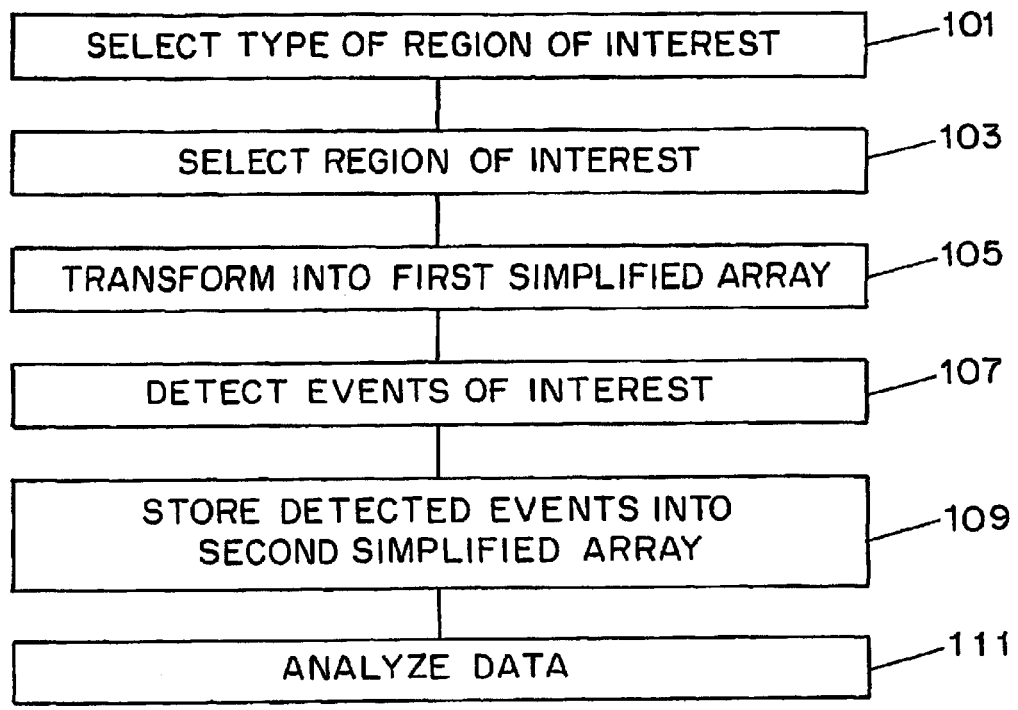
FIG. 1 illustrates a flow diagram of a method in accordance with the present invention.
Figure 2:
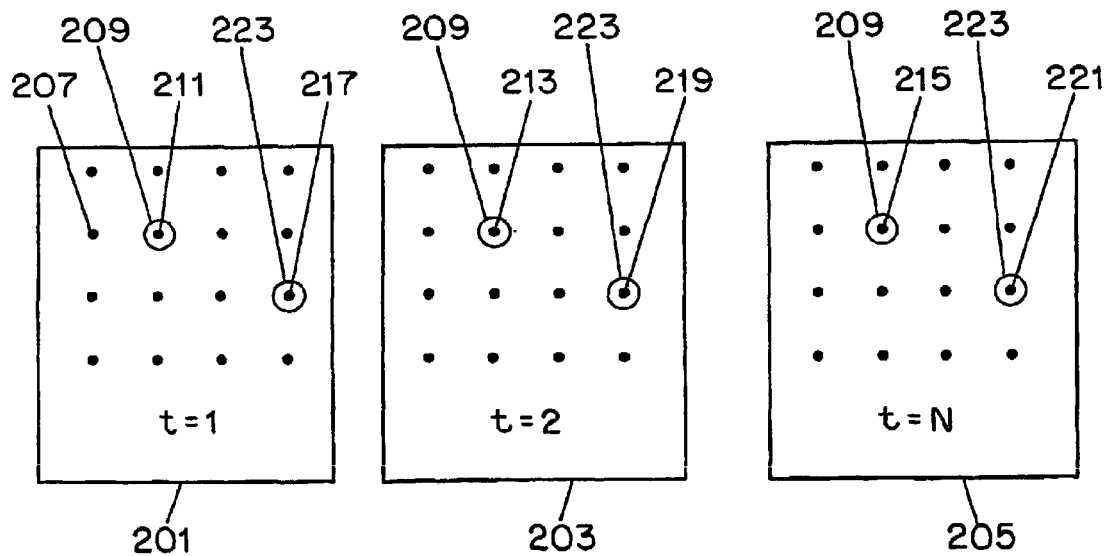
FIG. 2 illustrates an example sequence of data arrays for analyzing in accordance with the present invention.

Referring to FIG. 1, there is shown a flow diagram representing an exemplary method for analyzing a sequence of data arrays in accordance with the present invention. For purposes of this description, the sequence of data arrays operated upon corresponds to a series of two dimensional optical images of neuronal cell slices, such as a slice of brain tissue, captured at a fixed interval of time. Thus, the input data is a series of two dimensional data arrays, with each dimension corresponding to a spatial dimension and each element of the data array corresponding to fluorescence level or other optical measure of activity in the imaged neuronal cell slice. Each data array in the series corresponds to image data at a different instant in time, with the images taken at fixed intervals of time. The format of this input data will be discussed further herein with reference to FIG. 2. It will be understood that the present invention is not limited to such data. For example, the input data could correspond to expression levels of genes within a population of subjects.

Other potential input data sets will be apparent to one of ordinary skill in the art.

In the exemplary embodiment, performance of the method is assisted by a general purpose computer adapted to operate the MAC-OS operating system and to interpret program code written in Interactive Data Language ("IDL") version 5.1 or later, developed by Research Systems, Inc. The IDL program code of the exemplary embodiment is appended hereto as Appendices A, B and C described further herein. Other operating systems and programming languages could be used to perform the steps of the exemplary embodiment without departing from the scope of the invention, and the modifications necessary to make such a change will be apparent to one of ordinary skill in the art.

In step 101, a selection of at least one type of region of interest of the input data arrays is made. This selection may be made manually, automatically based on certain criteria relevant to the particular data being analyzed, or predetermined. In the exemplary embodiment, there is only one relevant type of region of interest, and that is predetermined to be a neuron in the image data. If other data were to be analyzed, the relevant type of region of interest may be different and there may be multiple such types of regions.

In step 103, a selection of one or more regions of interest for each of the selected types of regions of interest is made. To further understand this step in the exemplary embodiment, reference is made to FIG. 2 where an example of an input data array of a sequence of two dimensional image data is shown. Data array 201 is a array of picture element (pixel) data corresponding to an image acquired at time t=1. As can be seen, in this data array, there are sixteen pixels 207, each representing the optical intensity at a corresponding spatial region of the original image. Although only sixteen pixels are shown here, it will be understood that actual data will have many more pixels, corresponding to the resolution of the imaging device. In the preferred embodiment, the imaging device is a charge coupled device (CCD) camera which is capable of converting an optical image into digital pixel data.

A fixed interval of time after the image array 201 is acquired, second image array 203 is acquired. The process of acquiring data images continues at fixed intervals until final image array 205 is acquired at time t=N. In this example, time t=1 corresponds to the time the first image was take and time t=N corresponds to the time the last image was taken. The fixed time interval and number of images acquired (N) can be adjusted to maximize time resolution by reducing the fixed time interval. By reducing the time interval and increasing N, the amount of data collected will increase accordingly, which may lead to longer analysis times.

Returning to FIG. 1, the step of selecting a region of interest 103 consists of selecting an area of the image data where a neuron is present. For example, in FIG. 2, the circles 209 and 223 represent neurons in the original image data that are the regions of interest. Accordingly, the selecting step 103 consists of selecting the image data at pixel locations 211 and 217 as regions of interest. In the preferred embodiment, the step is performed manually by a user viewing an image corresponding to image data frame 201 or other image data frame and selecting the area where the neuron is visible. Because each image pixel data array in the input data sequence corresponds to the same spatial area over time, and because the neurons do not move over the time of observation, the pixels of interest in all subsequent images arrays can also be identified. Thus, in FIG. 2, it can be seen that pixel 219 in image pixel array 203 and pixel 221 in image pixel array 205 represent the same neuron as pixel 217 in image array 201. Similarly, pixels 211, 213, and 215 all represent the same neuron of interest.

Figure 3:
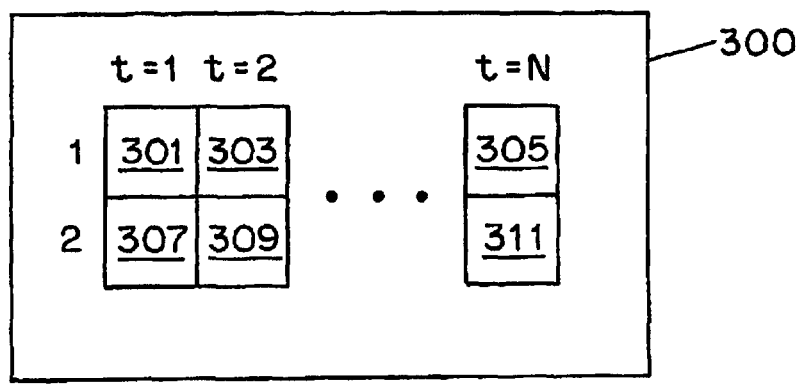
FIG. 3 illustrates an example of a simplified data structure generated by the method of FIG. 1.

In step 105, the data corresponding to the selected regions of interest are transformed into a simplified data array. This simplified data array contains only the pixel intensity data from the original sequence of pixel data arrays that corresponds to the regions of interest. An example of such a simplified data array is shown in FIG. 3. There, each data row corresponds to one of the selected regions of interest from the original sequence of pixel data arrays, while each column represents a different image pixel array in the original sequence of image pixel arrays. Each element in the simplified data array contains the intensity value of pixels in the relevant region of interest at a particular time. Thus, in step 105, the intensity data for pixel 211 in image pixel array 201 is placed in the portion of simplified data array 300 designated as array element 301, while pixel intensity data 217 is placed in array element 307. Similarly, pixel intensity data 213 and 219 are placed in array elements 303 and 309 respectively. The process continues until pixel intensity data 215 and 221 are placed in elements 305 and 311 respectively. It will be understood that if more than two neurons were selected in step 103, simplified array 300 would have more than 2 rows. If a neuron selected in step 103 spans more than one pixel position in the original sequence of image arrays, the average pixel intensity of the pixels corresponding to each selected neuron can be stored in the elements of simplified data array 300. If all of the data in the original sequence of data arrays corresponds to regions of interest, the transformation step would consists only of storing the input data into a data array having the dimensions described and no data from the original sequence need be ignored or discarded during the transformation step.

In step 107, events of interest in the simplified data array 300 are detected. In the exemplarly embodiment an event of interest is detected by calculating a statistical mean and standard deviation for all pixel intensity data corresponding to a particular region of interest. Thus, where the pixel intensity data is contained in the simplified array 300, a mean and standard deviation is calculated for all data pixel intensity in each row of the simplified array. An event is then detected where the pixel intensity data for a particular region of interest exceeds the mean for all data in the region of interest by a predetermined number of standard deviations. If activity were defined by a drop in intensity rather than an increase in intensity, the event could be detected by examining the pixel intensity data in a certain region of interest for an entry where the intensity is less than the mean for all data in the region of interest by a predetermined number of standard deviations. The number of standard deviations may be entered by a user before the calculations are preformed, or a default number may be used, such as two or three. In this fashion, the method will detect those instances in time where the pixel intensity is much higher than the average intensity, thus suggesting neuron activity has occurred.

In another exemplary embodiment, an event is detected by looking for pixel intensities that exceed previous pixel intensities of the same regions of interest by a threshold amount. Thus, for example, if the pixel intensity stored in data element 309 exceeded the pixel intensity stored in data element 307 by a certain percentage, an event is said to have occurred at the time corresponding to pixel position 307 (i.e. t=1). Again, if an event were indicated by a drop in intensity rather than an increase, the detection step would involve looking for pixel intensity that are less than previous pixel intensities of the same region of interest by the threshold amount. The threshold amount can be specified by a user before the calculations are performed, or a default number can be used such as twenty percent. The detection can occur over many time periods, for example, the data corresponding to the image taken at time t=6 could be compared to the image taken at time t=1 to see if an increase beyond the threshold amount has occurred. This would be useful to detect events that occur gradually over time rather than relatively instantaneously.

In step 109, the results of detection step 107 are stored in a second simplified array. For this purpose, the second simplified array is identical to the first simplified array illustrated in FIG. 3; however, the data stored in the second simplified array is binary rather than pixel intensity values. Thus, the entries in the second simplified array would be 1 or 0 (or yes or no), corresponding to whether an event of interest occurred in that region of interest at the corresponding time.

In step 111, the stored data is analyzed. In the preferred embodiment, the data is analyzed to determine whether various neurons are correlated (i.e. whether they are coactive), the strength of those correlations (i.e. how often they are coactive relative to how many times each neuron or one of the neurons is active), how significant the correlations are (i.e. whether the correlation is stronger than would be expected if from a random data set) and the behavior of the entire neuron population.

Figure 5:
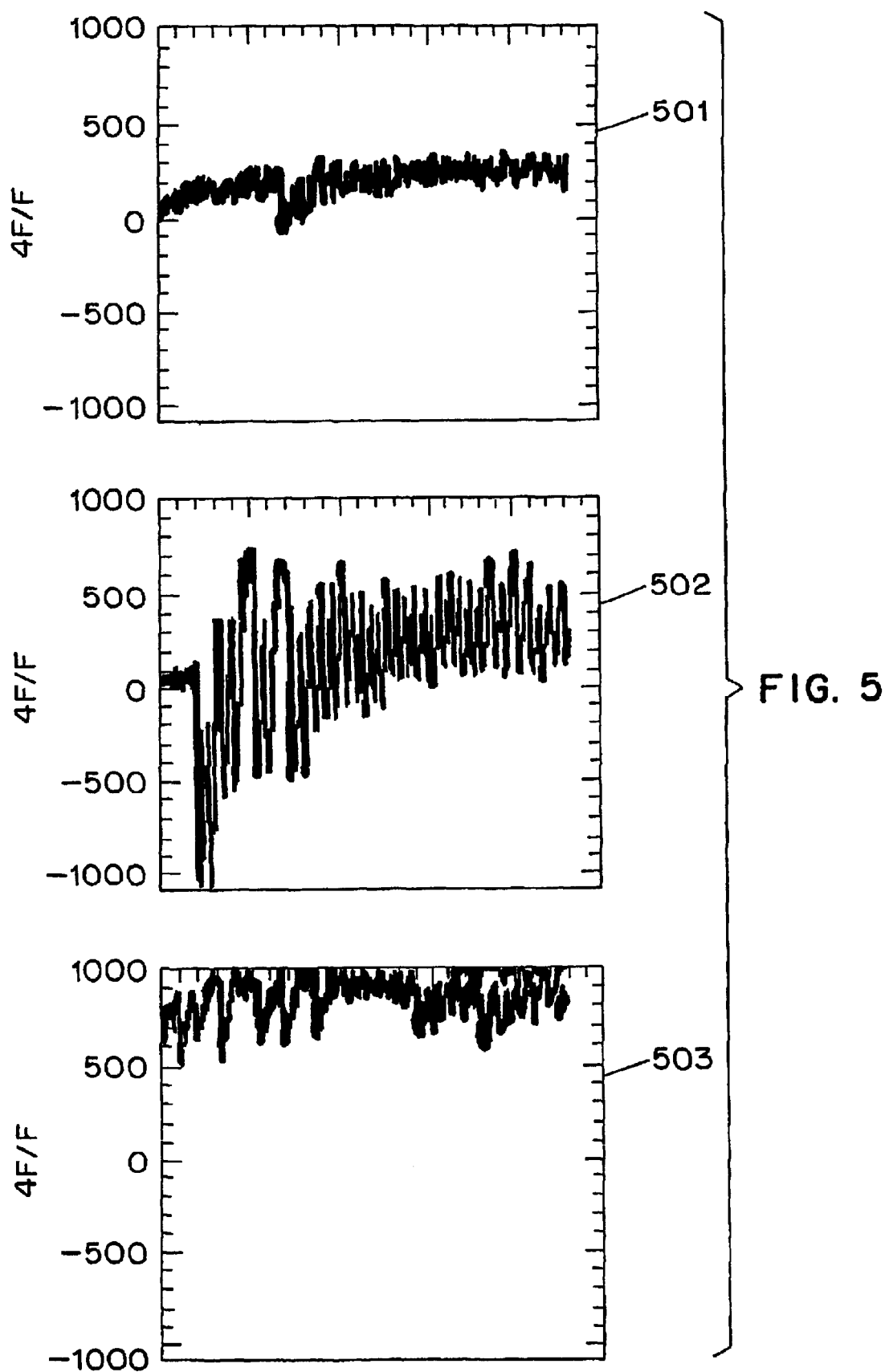
FIG. 5 illustrates a visual plot generated in accordance with the method of FIG. 1.

In the exemplary embodiment, the data is analyzed by plotting at least a portion of the data contained in the first simplified data array 300. For example, pixel intensity for one neuron can be plotted over time. Pixel intensities for all neurons could also be plotted over time, either in separate plot windows or superimposed on the same plot window. Additionally, the pixel intensities for all neurons could be averaged and plotted over time to show global behavior of the systems. FIG. 5 illustrates three possible plots 501, 502, 503 of pixel intensity over time.

Figure 4:
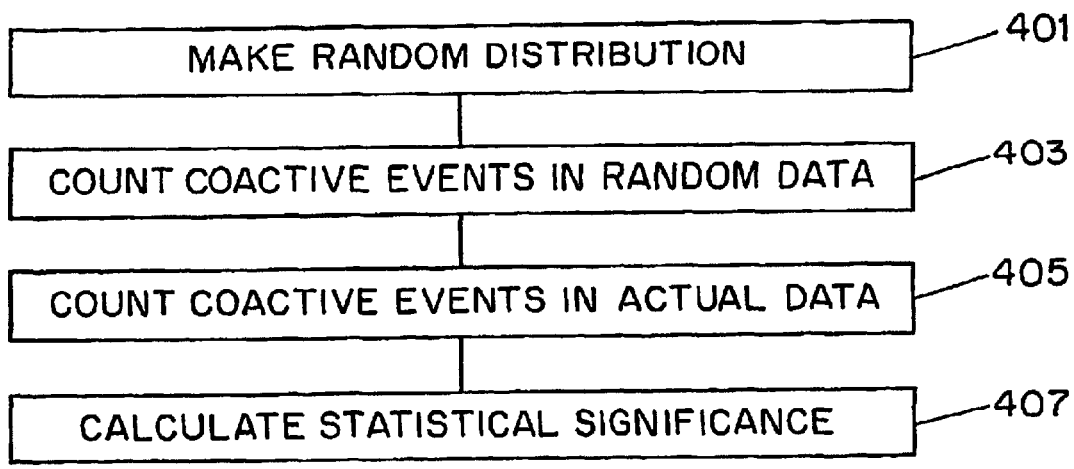
FIG. 4 illustrates a flow diagram of a method of analyzing data useful in the method of FIG. 1.

In another exemplary embodiment illustrated in FIG. 4, the data in the second simplified array is analyzed to determine the number of coactive events in the dataset and the statistical significance of those events. In step 401, a random distribution of neuron activity is generated. The random data is generated by shifting the data in each row of the second simplified array by a random amount. In step 403, the number of coactive events in the random dataset is counted. This process is repeated numerous time to generate a random distribution. The number of random trials may be set by the user or a default number of random trials may be conducted, such as 1000.

Counting coactive events for this purpose means counting all instances where two neurons are coactive. Coactive events for this purpose means events of interest that occurred in two neurons at the same time, or within a specified number of time intervals from each other. Thus, if the specified number of time intervals is one, then if a event occurred in neuron 1 at time t=1 301 and an event occurred in neuron 2 at time t=2 309, those events would be considered coactive. The time interval may be specified by a user before coactive events are counted, or may be a default setting such as two time intervals.

Once the random trials have been completed and a random distribution of coactive events generated, the actual number of coactive events in the data is calculated in step 405 using the same counting methodology was used to count coactive events in the random trials. The actual number of coactive events is then superimposed on a plot of the random distribution. The statistical significance of the coactive events is determined in step 407 by calculating the area under the distribution curve to the right of the number of actual coactive events in the data. This result, termed the "p-value" represents the probability that the number of detected coactive events in the actual data is produced by a random neuron activity.

In a further exemplary embodiment, a random distribution of activity is generated as previously described, except the only coactive events that are counted in steps 403 and 405 are those where a predetermined number of neurons are coactive. The predetermined amount of coactive neurons may be specified by a user or a predetermined default value such as four may be used. Additionally, it may be specified whether exactly that many coactive events must be present or at least that many coactive events must be present to be considered a coactive event for counting. Thus, the embodiment allows instances of multiple neurons active simultaneously (rather than simply two neurons active simultaneously) to be counted and the statistical significance of that number to be reported. In this exemplary embodiment, the random distribution and actual number of coactive events are plotted. The statistical significance of the actual number of coactive events is calculated using the formula: $C_{rand}/N_{rand}$ where $C_{rand}$ is the number of random trials that resulted in more coactive matches than the actual data set and $N_{rand}$ is the total number of random trials used to generate the random distribution, and is reported to a user. Additionally, a network map may be plotted showing the spatial locations of the coactive neurons with lines between those that were coactive. The spatial locations of the active neurons were those specified by the user during neuron selection step 103 in FIG. 1.

In a still further exemplary embodiment, a random distribution of neuron activity is generated as previously described except the only coactive events that are counted in steps 403 and 405 are those where at least two neurons are active a predetermined number times throughout the dataset. The number of times the two or more neurons must be active can be specified by a user or a default number such as two may be used. In this exemplary embodiment, the random distribution and actual number of coactive events are plotted. The statistical significance of the actual number of coactive events is calculated using the formula: $C_{rand}/N_{rand}$ where $C_{rand}$ is the number of random trials that resulted in more coactive matches than the actual data set and $N_{rand}$ is the total number of random trials used to generate the random distribution, and is reported to a user. Additionally, a network map may be plotted showing the spatial locations of the coactive neurons with lines between those neurons that were coactive the specified number of times. The spatial locations of the active neurons were those specified by the user during neuron selection step 103 in FIG. 1.

Figure 7:
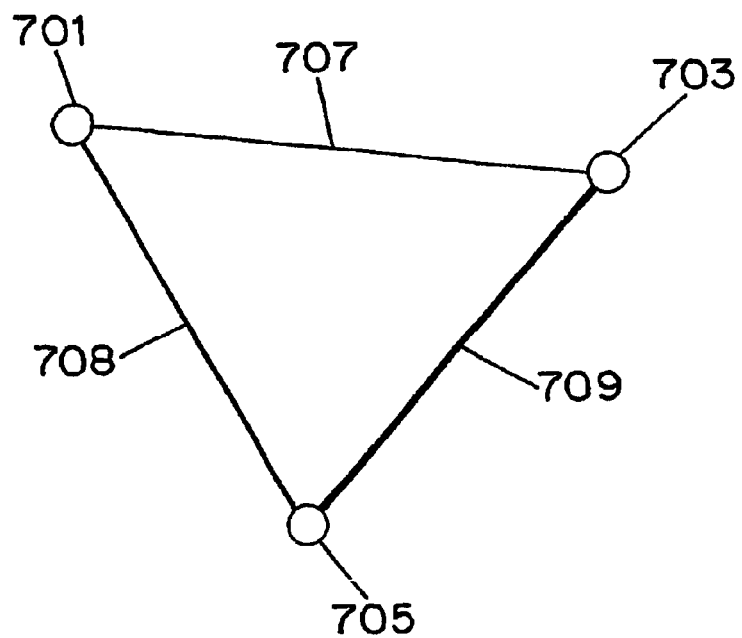
FIG. 7 illustrates a correlation map generated in accordance with the method of FIG. 1.

In yet another preferred embodiment, a correlation map is plotted. To plot the correlation map, a correlation coefficient array is first generated for all of the neurons. The correlation coefficients are defined as C(A,B)=number of times neuron A and B are coactive divided by the number of times neuron A is active. For this purpose, coactive means active at the same time, or within a specified number of time intervals of each other. The number of time intervals may be specified by a user or a default number such as one time increment may be used. The number of correlation coefficients will be equal to the square of the number of neurons selected in step 103 in FIG. 1. A correlation map is then drawn consisting of a map of all active neurons with lines between each pair of neurons having a line thickness proportional to the correlation coefficient of those two neurons. An example of such a correlation map is illustrated in FIG. 7. There, the thickness of line 707 is proportional to the magnitude of the correlation coefficient for neurons 701 and 703. Line 709, which appears thicker than line 707, indicates that the correlation between neurons 703 and 705 is stronger than the correlation between neurons 701 and 703. The correlation map may be superimposed on an image array selected from the original input data. If the correlation coefficient is below a predetermined threshold amount, the corresponding line may be omitted from the correlation map. The predetermined threshold amount may be specified by a user or a default threshold may be used.

Figure 6:
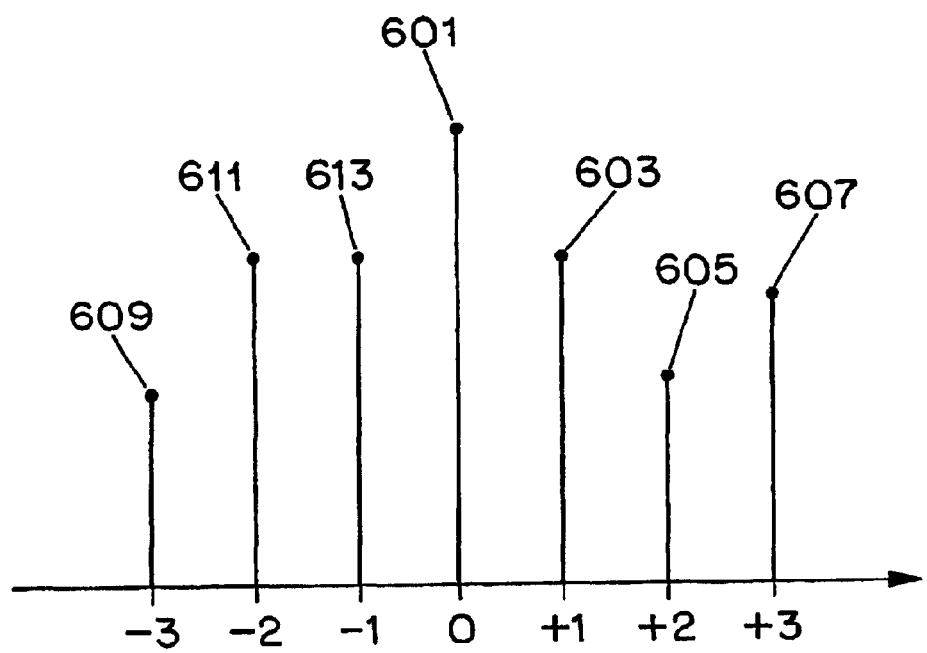
FIG. 6 illustrates a cross-correlogram generated in accordance with the method of FIG. 1.

In still another exemplary embodiment, a cross correlogram is drawn to show potential causality among neuron activity. This can be used to find neurons with events that consistently precede or follow events of another neuron. A cross correlogram simply creates a histogram of the time intervals between events in two specified neurons. A line of height proportional to the number of times the first neuron is active one time interval following activity by the second neuron is plotted at +1 on the x-axis of the histogram. A line of height proportional to the number of times the first neuron is active two time intervals following activity by the second neuron is plotted at +2 on the x-axis of the histogram, and so on. An example of such a cross correlogram is illustrated in FIG. 6. The line 601 represents the number of occasions the first and second neurons were coactive, while line 607 represents the number of times the first neuron was active three time intervals after the second neuron was active. A cross correlogram may be performed on a single neuron to detect temporal characteristics in the neuron's firing such as the fact that the neuron is active with a period of every three time intervals a certain number of times during the observation.

IDL code implementing all of the preceding steps of the exemplary embodiment is attached hereto as Appendix A. The procedure "multicell" and "multicell_event" are the main procedures. All relevant sub-procedures and functions are also included in Appendix A.

In another exemplary embodiment of step 111 in FIG. 1, the data is analyzed by finding a hidden Markov state sequence from the second simplified data array. This embodiment uses the principal of Hidden Markov modeling described in Rabiner, *A Tutorial on Hidden Markov Models and Selected Applications in Speech Recognition*, Proceedings of the IEEE, vol. 77 pp. 257–286 (1989). Essentially, a Markov model is a way of modeling a series of observations as functions of a series of Markov states. Each Markov state has an associated probability function which determines the likelihood of moving from that state directly to any other state. Moreover there is an associated initial probability matrix which determines the likelihood the system will begin in any particular Markov state. In a hidden Markov Model, the Markov states are not directly observable. Instead, each state has an associated probability of producing a particular observable event. A complete Markov model requires the specification of the number of Markov states (N); the number of producible observations per state (M); the state transition probability matrix (A), where each element $a_{ij}$ of A is the probability of moving directly from state i to state j; the observation probability distribution (B), where each element $b_i(k)$ of B is the probability of producing observation k while in state i; and the initial state distribution (P), where each element $p_i$ of P is the probability of beginning the Markov sequence in state i.

In the exemplary embodiment, it is assumed that the number of times a neuron is active within each Markov state follows the Poisson distribution. Thus, each neuron in each state has an associated Poisson Lambda parameter, which can be understood in the exemplary embodiment to correspond to the neuron's average firing rate within the given Markov state. The set of all of these Lambda parameters is then assumed to be the B matrix. Given estimations of the Markov Model parameters, the method uses the Viterbi algorithm to find the single best state sequence, i.e. the state sequence that most likely occurred to generate the observed results. The parameter N may be selected by the user or a default number such as 4 states may be used. The Viterbi algorthim is described as follows:

Initialization $$\delta_1(i) = p_i b_i(O_1) \; 1 \leq i \leq N,$$

$$\psi_1(i) = 0,$$

where $\delta_t(i)$ is the highest probability along a single path at time t that accounts for the first t observations and ends in state i, and $\psi$ is used to store the argument which maximizes $\delta_t(i)$.

Recursion:

$$\delta_t(j) = \max_{1 \leq i \leq N} [\delta_{t-1}(i) a_{ij}] b_i(O_i) \quad 2 \leq i \leq T$$
$$1 \leq j \leq N,$$
$$\psi_t(j) = \mathrm{argmax}_{1 \leq i \leq N} [\delta_{t-1}(i) a_{ij}] \quad 2 \leq t \leq T$$
$$1 \leq j \leq N,$$

Termination:

$$p^* = \max_{1 \leq i \leq N} [\delta_T(i)],$$
$$q_T^* = \mathrm{argmax}_{1 \leq i \leq N} [\delta_T(i)],$$

Path (Backtracking):

$$q_t^* = \psi_{t+1}(q_{t+1}^*) t = T-1, T-2, \ldots, 1.$$

Once a possible state sequence is generated, a cross-correlogram between neurons in a predetermined state can be plotted using the methodology previously described. The state may be selected by the user or a default state such as the first state may be used.

IDL code implementing the preceding embodiment involving the hidden Markov model is attached hereto as Appendix B. The procedure "hidden_markov" and "hidden_markov_event" are the main procedures. All relevant sub-procedures and functions are also included in Appendix B.

In another exemplary embodiment the data is analyzed by performing a singular valued decomposition (SVD) on the data in the first simplified array formed in step 105. In this embodiment, steps 107 and 109 may be skipped. In a singular valued decomposition, the data set is reduced from N dimensions, where N is the number of selected neurons, to d dimensions, where d is specified and is less than N. The SVD algorithm, which is well known to one of ordinary skill in the art and is specified in the code in Appendix C, fits the observed data to a data model that is a linear combination of any d number of functions of the spaces of data (such as time and location). The SVD algorithm discards the eigenmodes corresponding to the smallest N-d eigenvalues. In this embodiment, the result that is plotted for visual analysis is the level of each neuron's contribution to each of the calculated d modes where a higher contribution to the mode is a larger number on the y-axis of the plot.

In a further exemplary embodiment not shown in FIG. 1, the SVD calculation described may be performed on the data in the first simplified data array before step 107. The data corresponding to the first eigenmode of the SVD, which will often correspond to noise in the original data, may then be removed from the first simplified data array. The modified first simplified data array, with noise removed, may then be processed beginning with step 107 in FIG. 1 as previously described. In this fashion, the data analysis, such as the HMM analysis could be performed on data with less noise, generating more useful results.

IDL code implementing the preceding embodiment involving the singular value decomposition algorithm is attached hereto as Appendix C. The procedure svd_gui and svd_gui_event are the main procedures. All relevant sub-procedures and functions are also included in Appendix C.

Although the present invention has been described in detail, it should be understood that various changes, substitutions and alterations can be made hereto without departing from the scope or spirit of the invention as defined by the appended claims.

What is claimed is:

1. A method for analyzing a sequence of data arrays representative of tissue slice images or gene expression information comprising the steps of:
    (a) selecting at least one type of region of interest of said data arrays;
    (b) selecting at least one region of interest for each of said at least one selected type of region of interest selected in step (a) from said data arrays;
    (c) transforming said sequence of data arrays into a first simplified data array having a first dimension equal to the number of said at least one region of interest selected in step (b), a second dimension equal to the number of data arrays in said sequence, and a third dimension equal to the number of said selected types of regions of interest;
    (d) detecting events of interest in said at least one selected region of interest;
    (e) storing said detected events of interest in a second simplified data array of binary data, having the same dimensions as said first simplified data array; and
    (f) analyzing data in one of the data arrays selected from the group consisting of said first simplified data array and said second simplified data array, to determine relationships between said detected events of interest.

2. The method of claim 1, wherein said sequence of data arrays comprises a series of two dimensional arrays corresponding to a time series of two dimensional observations of an object.

3. The method of claim 1, wherein said object is neuronal cell slice containing a plurality of neurons and wherein said step of selecting a region of interest comprises selecting one or more neurons in said series of two dimensional observations.

4. The method of claim 2, wherein one type of region of interest is selected in step (a) and wherein said step of selecting at least one region of interest comprises selecting at least one portion of said sequence of data arrays that corresponds to a particular spatial region of said two dimensional observations of said object.

5. The method of claim 4, wherein said transforming step comprises extracting data from each array in said sequence of data arrays that corresponds to said particular spatial region of interest and storing said data in said first simplified array, each data entry having an associated first dimensional index and an associated second dimensional index, wherein said first dimensional index is between one and the number of spatial regions corresponding to said selected regions of interest of said sequence of data arrays, and said second dimensional index is between one and the number of two dimensional observations of said object in said sequence of data arrays.

6. The method of claim 5, wherein said step of detecting events of interest comprises
    calculating a statistical mean and statistical standard deviation from a data population consisting of all entries in said first simplified array having identical first dimensional indexes, for each of said first dimensional indexes;
    determining for each entry in said first simplified array whether said entry exceeds, by a predetermined number of said standard deviation associated with said entry, the mean associated with said entry and denominating such a data entry an event.

7. The method of claim 6, wherein entries in said second simplified data array have the same associated first and second dimensional indexes as corresponding entries in said first simplified data array and wherein said storing said detected events of interests comprises storing a one in said second simplified array when the data entry with the corresponding first and second dimensional indexes in said first simplified array is denominated an event and storing a zero in said second simplified array otherwise.

8. The method of claim 5, wherein said detecting events of interest comprises determining whether a first data entry in said first simplified array exceeds, by a threshold amount, a second data entry in said first simplified array wherein said second data entry has an identical first dimensional index as said first data entry and a second dimensional index corresponding to an earlier point in time than said first data entry and denominating said second data entry an event.

9. The method of claim 8, wherein entries in said second simplified data array have the same associated first and second dimensional indexes as corresponding entries in said first simplified data array and wherein said storing said detected events of interests comprises storing a one in said second simplified array when the data entry with the corresponding first and second dimensional indexes in said first simplified array is denominated an event and storing a zero in said second simplified array otherwise.

10. The method of claim 1, wherein said step of analyzing comprises plotting at least a portion of said data in said first simplified data for visual analysis.

11. The method of claim 1, wherein said step of analyzing comprises detecting said events of interest that are coactive and determining whether the number of coactive events is statistically significant.

12. The method of claim 11, wherein said step of detecting events of interest that are coactive comprises detecting instances where said events of interest are detected in two or more of said regions of interest simultaneously.

13. The method of claim 11, wherein said step of detecting events of interest that are coactive comprises detecting instances were events of interest are detected in two of said regions of interest simultaneously at a plurality of locations along said second dimension of said second simplified data array.

14. The method of claim 1, wherein said step of analyzing comprises calculating a strength of correlation between at least two regions of interest based on the number of coactive events of interest occurring in said at least two regions of interest and displaying a correlation map illustrating the strength of correlation between said regions of interest by lines connecting said regions of interest wherein the thickness of each of the lines is proportional to said calculated strength of correlation between respective regions of interest connected by the line.

15. The method of claim 1, wherein said step of analyzing comprises displaying a cross-correlogram between events of interest occurring in at least one of said regions of interest.

16. The method of claim 1, wherein said step of analyzing comprises detecting at least one hidden Markov state sequence from said second simplified data array.

17. The method of claim 16, wherein said step of analyzing further comprises displaying a cross-correlogram between events of interest occurring in one of said regions of interest while said region of interest is in one of said detected hidden Markov states.

18. The method of claim 1, further comprising:
before said step of detecting, performing a singular valued decomposition on said data in said first simplified data array to calculate a predetermined number of eigenmodes;
modifying said data in said first simplified data array by removing the data that corresponds to the first of said predetermined number of eigenmodes; and
storing said modified data into said first simplified data array.

19. A method for analyzing a sequence of data arrays representative of tissue slice images or gene expression information comprising the steps of:
(a) selecting at least one type of region of interest of said data arrays;
(b) selecting at least one region of interest for each of said at least one type of region of interest selected in step (b) from said data arrays;
(c) transforming said sequence of data arrays into a first simplified data array having a first dimension equal to the number of said selected regions of interest, a second dimension equal to the number of data arrays in said sequence, and a third dimension equal to the number of said selected types of regions of interest; and
(d) performing a singular valued decomposition on said first simplified data array to determine relationships between said regions of interest.

20. A system for analyzing a sequence of data arrays representative of tissue slice images or gene expression information comprising in a data processor:
a region type selector for selecting at least one type of region of interest of said data arrays;
a region selector for selecting at least one region of interest for each of said selected type of region of interest from said data arrays;
a first data transformer for transforming said sequence of data arrays into a first simplified data array having a first dimension equal to the number of said selected regions of interest, a second dimension equal to the number of data arrays in said sequence, and a third dimension equal to the number of said selected types of regions of interest;
an event detector for detecting events of interest in said regions of interest;
a second data transformer for storing said detected events of interest into a second simplified data array of binary data, having the same dimensions as said first simplified data array; and
a data analyzer for analyzing data in one of the data arrays selected from the group consisting of said first simplified data array and said second simplified data array, to determine relationships between said detected events of interest.

21. The system of claim 20, wherein said sequence of data arrays comprises a series of two dimensional arrays corresponding to a time series of two dimensional observations of an object.

22. The system of claim 21, wherein said object is neuronal cell slice containing a plurality of neurons and wherein said step of selecting a region of interest comprises selecting one or more neurons in said series of two dimensional observations.

23. The system of claim 21, wherein said region type selector selects one type of region of interest and wherein said region selector selects at least one portion of said sequence of data arrays that corresponds to a particular spatial region of said two dimensional observations of said object.

24. The system of claim 23, wherein said region selector receives coordinates corresponding to said particular spatial region from a user.

25. The system of claim 23, wherein said first data transformer extracts data from each array in said sequence of data arrays that corresponds to said particular spatial region of interest and stores said data in said first simplified array, wherein each data entry in said first simplified array has an associated first dimensional index and an associated second dimensional index, wherein said first dimensional index is between one and the number of spatial regions corresponding to selected regions of interest of said sequence of data arrays and said second dimensional index is between one and the number of two dimensional observations of said object in said sequence of data arrays.

26. The system of claim 25, wherein said event detector further comprises:
a statistical calculator for calculating a statistical mean and statistical standard deviation from a data population consisting of all entries in said first simplified data array having identical first dimensional indexes, for each of said first dimensional indexes; and
a comparator for determining for each entry in said first simplified array whether said entry exceeds, by a predetermined number of said standard deviations associated with said entry the mean associated with said entry and denominating such a data entry an event.

27. The system of claim 26, wherein said second data transformer stores entries in said second simplified data array having the same associated first and second dimensional index as corresponding entries in said first simplified data array and wherein said second data transformer stores a one in said second simplified array when the data entry with corresponding first and second dimensional indexes in said first simplified array is denominated an event and stores a zero in said second simplified data array otherwise.

28. The system of claim 25, wherein said event detector determines whether a first data entry in said first simplified array exceeds, by a threshold amount, a second data entry in said first simplified data array, wherein said second data entry has an identical first dimensional index as said first data entry and a second dimensional index corresponding to an earlier point in time than said first data entry, and denominates said second data entry an event.

29. The system of claim 28, wherein said second data transformer stores entries in said second simplified data array having the same associated first and second dimensional index as corresponding entries in said first simplified data array and wherein said second data transformer stores a one in said second simplified array when the data entry with corresponding first and second dimensional indexes in said first simplified array is denominated an event and stores a zero in said second simplified data array otherwise.

30. The system of claim 20, wherein said data analyzer plots at least a portion of said data in said first simplified array for visual analysis.

31. The system of claim 20, wherein said data analyzer detects said events of interest that are coactive and determines whether the number of coactive events is statistically significant.

32. The system of claim 31, wherein said data analyzer detects said events of interest that are coactive comprises operability to detect instances where said events of interest are detected in two or more of said regions of interest simultaneously.

33. The system of claim 31, wherein said data analyzer detects instances where events of interest are detected in two of said regions of interest simultaneously at a plurality of locations along said second dimension of said second simplified data array.

34. The system of claim 20, wherein said data analyzer calculates a strength of correlation between at least two regions of interest based on the number of coactive events of interest occurring in said at least two regions of interest and displays a correlation map illustrating the strength of correlation between said regions of interest by lines connecting said regions of interest wherein the thickness of each of the lines is proportional to said calculated strength of correlation between respective regions of interest connected by the line.

35. The system of claim 20, wherein said data analyzer displays a cross-correlogram between events of interest occurring in at least one of said regions of interest.

36. The system of claim 20, wherein said data analyzer detects at least one hidden Markov state sequence from said second simplified data array.

37. The system of claim 36, wherein said data analyzer displays a cross-correlogram between events of interest occurring in one of said regions of interest while said region of interest is in one of said detected hidden Markov states.

38. The system of claim 20, wherein said system further comprises:
 a decomposer to perform a singular valued decomposition on said data in said first simplified data array and calculating a predetermined number of eigenmodes;
 a data modifier for modifying said data said first simplified data array by removing the data that corresponds to the first of said predetermined number of eigenmodes; and
 data storage for storing said modified data into said first simplified data array.

39. A system for analyzing a sequence of data arrays representative of tissue slice images or gene expression information comprising in a data processor:
 a region type selector for selecting at least one type of region of interest of said data arrays;
 a region selector for selecting at least one region of interest for each of said selected type of region of interest from said data arrays;
 a first data transformer for transforming said sequence of data arrays into a first simplified data array having a first dimension equal to the number of said selected regions of interest, a second dimension equal to the number of data arrays in said sequence, and a third dimension equal to the number of said selected types of regions of interest;
 a decomposer for performing a singular value decomposition on said first simplified data array to determine relationship between said regions of interest.

* * * * *

UNITED STATES PATENT AND TRADEMARK OFFICE
CERTIFICATE OF CORRECTION

PATENT NO. : 6,823,286 B2
DATED : November 23, 2004
INVENTOR(S) : Yuste et al.

It is certified that error appears in the above-identified patent and that said Letters Patent is hereby corrected as shown below:

Column 9,
Line 57, "is neuronal" should read -- is a neuronal --

Column 11,
Lines 39-40, "at least one type of region of interest selected in step (b) from said data arrays;" should read -- at least one type of region of interest selected in step (a) from said data arrays; --

Signed and Sealed this

Twelfth Day of April, 2005

JON W. DUDAS
*Director of the United States Patent and Trademark Office*